(12) United States Patent
Lötters et al.

(10) Patent No.: US 9,857,321 B2
(45) Date of Patent: Jan. 2, 2018

(54) DEVICE AND METHOD FOR DETERMINING THE COMBUSTION VALUE OF A FUEL

(71) Applicant: BERKIN B.V., Ruurlo (NL)

(72) Inventors: Joost Conrad Lötters, Ruurlo (NL); Theodorus Simon Josef Lammerink, Enschede (NL); Remco John Wiegerink, Hengelo (NL); Albertus Johannes Mouris, Purmerend (NL); Marco Gábor Pap, Ruurlo (NL); Meint Jelle De Boer, Ruurlo (NL); Remco Gerardus Petrus Sanders, Ruurlo (NL)

(73) Assignee: BERKIN B.V., Ruurlo (NL)

( * ) Notice: Subject to any disclaimer, the term of this patent is extended or adjusted under 35 U.S.C. 154(b) by 237 days.

(21) Appl. No.: 14/654,978

(22) PCT Filed: Dec. 24, 2013

(86) PCT No.: PCT/NL2013/050956
§ 371 (c)(1),
(2) Date: Jun. 23, 2015

(87) PCT Pub. No.: WO2014/104889
PCT Pub. Date: Jul. 3, 2014

(65) Prior Publication Data
US 2016/0195482 A1 Jul. 7, 2016

(30) Foreign Application Priority Data

Dec. 27, 2012 (NL) ........................... 2010064

(51) Int. Cl.
*G01N 25/28* (2006.01)
*G01N 25/32* (2006.01)
*G01N 33/22* (2006.01)

(52) U.S. Cl.
CPC ............. *G01N 25/28* (2013.01); *G01N 25/32* (2013.01); *G01N 33/225* (2013.01)

(58) Field of Classification Search
CPC ........ G01N 33/22; G01N 31/12; G01N 33/00; G01N 33/225; G01N 33/0013;
(Continued)

(56) References Cited

U.S. PATENT DOCUMENTS 4,433,922 A * 2/1984 Bohl ..................... G01N 33/225
374/36
2009/0013759 A1* 1/2009 Knobloch ............ G01N 33/225
73/25.05

FOREIGN PATENT DOCUMENTS

DE 102006042618 3/2008
EP 0098716 1/1984
(Continued)

*Primary Examiner* — Manish S Shah
(74) *Attorney, Agent, or Firm* — Casimir Jones S.C.

(57) ABSTRACT

The invention relates to a device (1) for determining the combustion value of a fuel. The device (1) comprises a fuel inlet (40) for supplying the fuel to be measured to the device (1). A gas inlet (50) is provided for supplying an oxygen-containing gas to the device (1). The device (1) further comprises a combustion unit connected to the fuel inlet (40) and the gas inlet (50), which combustion unit is provided with a combustion chamber (7) for combusting the fuel to be measured therein. A gas outlet (8) connected to the combustion chamber (7) makes it possible to discharge the combusted gas. The device (1) according to the invention comprises a flow measurement unit (14), preferably of the Coriolis type, disposed between the fuel inlet (40) and the combustion chamber (7).

19 Claims, 2 Drawing Sheets

Figure 1:
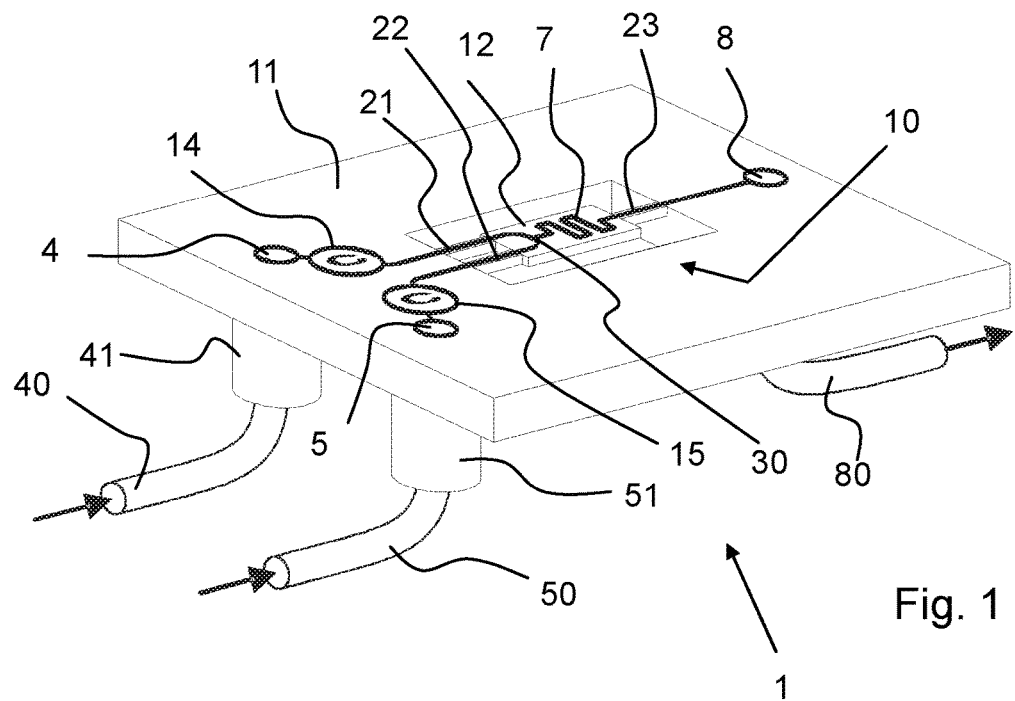

(58) Field of Classification Search
CPC ........ G01N 25/54; G01N 25/00; G01N 25/30; G01N 25/20; G01K 7/02; G01K 7/22; G01K 13/02; G01K 2205/04; G01K 2013/024; H01R 4/023; H01R 4/029; H01R 43/28
See application file for complete search history.

(56) References Cited

FOREIGN PATENT DOCUMENTS

| | | | |
|---|---|---|---|
| EP | 0623818 | 11/1994 | |
| EP | 1719983 | 11/2006 | |
| EP | 2015058 | 1/2009 | |
| EP | 2078936 | 7/2009 | |
| GB | 1103361 | 2/1968 | |
| NL | EP 2078936 A1 * | 7/2009 | ........... G01F 1/6845 |
| WO | 01/61285 | 8/2001 | |

* cited by examiner

DEVICE AND METHOD FOR DETERMINING THE COMBUSTION VALUE OF A FUEL

The present invention relates to a device and a method for determining the combustion value of a fuel. The combustion value of a fuel is in this regard defined as the amount of energy that is released upon (complete) combustion of that fuel.

A known device for determining the combustion value of a fuel is the bomb calorimeter as known, for example, from EP 0 623 818 A1. Said bomb calorimeter comprises a closed container, in which a precisely determined mass of the fuel to be measured, an oxygen-containing gas and an igniter are provided. The inner container is surrounded by an outer container, in which water is present. With the bomb calorimeter, the fuel to be measured is ignited together with the oxygen-containing gas. The fuel will combust. The heat that is released will heat the water in the outer container. The combustion value of the fuel can be determined by measuring the temperature increase of the water that results from the combustion.

In practice there is a need for an inexpensive and reliable manner of measuring the combustion value of fuels, in particular gaseous fuels, wherein preferably a manageable device can be used, so that measurements can be carried out also on site, for example at a new natural gas field, a shale gas field or a biogas plant.

Accordingly it is an object of the present invention to provide an improved device and method for determining the combustion value of a fuel.

In order to achieve that object, the invention provides a device of the kind described above, comprising a fuel inlet with an intake opening for supplying the fuel to be measured to the device;

a gas inlet with an intake opening for supplying an oxygen-containing gas to the device;

a combustion unit connected to the fuel inlet and the gas inlet, which combustion unit is provided with a combustion chamber for reacting the fuel to be measured with the oxygen containing gas in a combustion reaction therein;

a gas outlet connected to the combustion chamber for discharging waste gases produced in the combustion reaction; as well as means for measuring at least a measure of the amount of energy released by the combustion;

a flow measurement unit disposed between the intake opening of the fuel inlet and the combustion chamber.

Using the device according to the present invention it becomes possible to supply the fuel to be measured to the device in a continuous manner, mix said fuel with the oxygen-containing gas being supplied and subsequently combust the fuel (whether or not continuously), and thus determine the combustion value of the fuel. This makes it possible to measure variations in the combustion value, for example caused by a non-homogeneous fuel. It is also possible to precisely adapt the supply of the oxygen-containing gas to the amount of fuel being supplied so as to thus achieve complete combustion. Furthermore it becomes possible to supply a relatively small amount of fuel to the combustion chamber, which may thus be relatively small, so that a relatively small sample can be used for determining the combustion value. This means that a relatively small device can be used, so that the need for measurement on site is met and the object of the present invention is achieved.

In one embodiment, which will also be explained hereinafter, it is possible to provide a device having dimensions in the order of 0.1×0.1×0.1 m. This is a significant reduction in comparison with known systems, which in some cases have dimensions in the order of 1×1×1 m. Because the device according to the invention can be so small, a relatively small sample will suffice as well. Thus, a flow rate of 1 to 2 ml per minute will suffice in a small embodiment, whilst a flow rate of as much as 5000 ml per minute is needed with the known large systems.

The device according to the invention preferably comprises a flow measurement unit for determining the density and/or the flow rate of the fuel. A suitable flow measurement unit is a flow measurement unit of the Coriolis type, for example, whose construction and operation are known per se, as follows from EP 1 719 983, for example, whose contents are fully incorporated in the present application by reference. Using such a flow measurement unit, the flow rate (mass flow and/or volume flow) of the fuel to be measured can be determined in a relatively inexpensive and reliable manner. Said determination can take place just before the fuel reaches the combustion chamber, which will further increase the precision of the device. Additionally, the flow measurement unit of the Coriolis type is suitable for determining the density of the fuel to be measured while the fuel to be measured is being supplied. Thus it becomes possible to measure the density also momentarily, so that variations in said density can be taken into account in the determination of the combustion value, if desired, which further increases the precision. The use of the aforesaid flow measurement unit, for example of the Coriolis type, makes it possible to realise a relatively compact flow measurement unit, so that the entire device can be relatively small. Another advantageous aspect is the fact that such a sensor is relatively inexpensive. The flow measurement unit of the Coriolis type thus makes it possible to realise a compact and manageable construction, and in addition to that it is relatively inexpensive.

An additional advantage of a flow measurement unit of the Coriolis type is that it is very suitable for measuring the flow rate and/or the density both of a gaseous fuel and of a liquid fuel, or even of combinations thereof. Thus it is possible to determine the combustion value both of gaseous and of liquid fuels.

If the density of the fuel to be measured is measured, it is possible to determine the so-called Wobbe index WI (MJ/Nm$^3$) of the fuel in an efficient manner. The Wobbe index is used for comparing the combustion value of fuel gases of different composition. The Wobbe index can be calculated from:

$$WI = \frac{H}{\sqrt{G_S}}$$

where H [MJ/Nm$^3$] is the amount of heat or, in other words, the combustion value, that is generated during a complete combustion of a particular volume amount of the fuel gas with air; and $G_s$ [–] is the ratio between the mass densities of the fuel gas (for example to be determined by means of the flow measurement unit of the Coriolis type) and air, at the same temperature and the same pressure. The Wobbe index is a measure of the interchangeability of different gases on a particular burner. Gases having the same Wobbe index provide the same thermal capacity on a given burner. A burner set for a particular fuel gas will only retain its thermal capacity in the case of a changeover to a different gas composition if the Wobbe index of the gas does not change too much. If the difference in the Wobbe index is too large, the burner will no longer function properly and need readjusting. In practice a fluctuation of 5% is still considered to be acceptable for industrial uses; for household use a bandwidth of less than 2% applies.

In order to be able to determine also the Wobbe index with the device itself, the device, in one embodiment thereof, comprises means for determining the Wobbe index of the fuel, preferably on the basis of the density obtained by means of the flow measurement unit, for example of the Coriolis type. The combustion value H (MJ/Nm$^3$) as described above can be used in this regard.

To determine a measure of the combustion value of the fuel to be measured, it is preferred to measure a temperature increase resulting from the combustion. In one embodiment this can be realised in that the device is provided with at least one temperature measuring element which may be disposed on or near the combustion unit. The means for measuring at least a measure of the amount of energy released upon combustion thus comprise a temperature measuring element. In one embodiment, the temperature measuring element is disposed at a distance from the combustion chamber, such that the temperature measuring element will be exposed to smaller temperature increases. The temperature measuring element may be an integrated platinum resistance sensor.

In one embodiment, the device comprises a further flow measurement unit, for example of the Coriolis type, disposed between the intake opening of the gas inlet and the combustion chamber. The mass flow of the oxygen-containing gas can be determined and possibly controlled by using said flow measurement unit. Alternatively or additionally it is possible to determine the density of the oxygen-containing gas therewith, such that the Wobbe index can be more precisely determined therewith.

Reliable combustion of the fuel to be measured is obtained if the device is provided with a heating element for increasing the temperature of at least the fuel to be measured, preferably before it reaches the combustion chamber. The heating element, for example in the form of a resistance heating element, makes it possible to preheat the fuel to be measured and/or the oxygen-containing gas to an elevated temperature, for example to about 600° C., or another value, depending on the combustion temperature of the fuel to be measured. When the fuel is mixed with the oxygen-containing gas, an elevated temperature often suffices for obtaining spontaneous combustion. Possibly, additional, external heating elements may be provided, which further heat the mixture so as to effect spontaneous combustion. Also other combustion means may be provided.

A very compact, small embodiment of the device is obtained if it comprises a system chip with a silicon substrate provided on a carrier, wherein the system chip is provided with the flow measurement unit and/or the combustion unit. An embodiment with a flow measurement unit is described in EP 2 078 936, for example, which publication is fully incorporated in the present application by reference. With such an embodiment, it becomes possible to use a sensor the size of a chip, in the order of 2×2 cm, so that a considerable reduction in comparison with known systems is obtained. Advantageous is the fact that a flow measurement unit of the Coriolis type is suitable for being integrated with existing technology in the system chip.

The system chip may be provided with an opening within which a silicon nitride flow tube is present, which silicon nitride flow tube has two ends which each merge, via a wall of the opening, into a silicon nitride-coated channel in the silicon substrate, which embodiment is very suitable for the flow measurement unit of the Coriolis type.

In a very compact embodiment, which is in particular suitable for measuring the flow rate and/or the density of a gaseous fuel, the flow measurement unit of the Coriolis type comprises the silicon nitride flow tube. Because said flow tube is relatively thin-walled and the mass of the tube is thus relatively small, precise measurement of gases becomes possible as well.

It is conceivable that the combustion unit comprises the silicon nitride flow tube, and that, possibly additionally, the silicon nitride flow tube comprises the combustion chamber. The silicon nitride is very suitable for this purpose, because it is capable of withstanding temperatures of up to about 1000° C. In this way a compact construction is obtained, and this certainly applies if additionally the flow measurement unit of the Coriolis type comprises a further silicon nitride flow tube, as already described above.

The aspect of a relatively small combustion chamber, which is provided on a chip, is applicable per se, and the applicant reserves the right to protect this aspect, for example in one or more divisional applications. According to this aspect, there is provided a device for determining the combustion value of a fuel, the device comprising:
- a fuel inlet with an intake opening for supplying the fuel to be measured to the device;
- a gas inlet with an intake opening for supplying an oxygen-containing gas to the device;
- a system chip with a silicon substrate provided on a carrier, wherein the system chip is provided with a combustion unit connected to the fuel inlet and the gas inlet, which combustion unit is provided with a combustion chamber for chemically reacting the fuel to be measured with the oxygen containing gas in a combustion reaction therein;
- a gas outlet connected to the combustion chamber for discharging waste gases produced in the combustion reaction; as well as
- means for measuring at least a measure of the amount of energy released by the combustion.

In order to be able to obtain a precise measurement of the temperature increase effected by the combustion, the combustion chamber may be thermally insulated within the opening of the system chip. The amount of heat that is produced will in that case spread in the combustion unit itself through conduction and effect a temperature increase at the location of the temperature measuring element that is provided for that purpose. Said temperature increase will in that case be a measure of the amount of heat released from the fuel to be measured and thus of the combustion value.

It is preferable if complete combustion is achieved, such that a precise determination of the combustion value and/or of the Wobbe index will be possible. In one embodiment, the device therefore comprises a mixing element for mixing the fuel to be measured and the oxygen-containing gas.

In order to be able to check the degree of combustion, an oxygen sensor may in one embodiment be provided downstream of the combustion chamber for determining a measure of the amount of residual oxygen in the combustion gas. Alternatively or additionally, catalytic detection of non-combusted components may take place. Such an embodiment can be of relatively simple and compact construction.

In one embodiment, the device comprises a catalyst element. Using this catalyst element, the spontaneous combustion temperature can be reduced significantly, for example to 300° C., such that the temperature in the entire device, and in particular in the combustion unit, will be lower, which will have an advantageous effect on the life of the device.

According to one aspect, the invention provides a method for determining the combustion value of a fuel, using a device according to the invention, comprising the steps of:
supplying a fuel to be measured to the fuel inlet;
determining at least one parameter, such as the flow rate and/or the density of the fuel to be measured, by means of the flow measurement unit, which is preferably of the Coriolis type;
supplying an oxygen-containing gas to the gas inlet;
supplying the fuel to be measured as well as the oxygen-containing gas to the combustion chamber of the combustion unit;
reacting the fuel to be measured with the oxygen-containing gas in a combustion reaction therein; and also
determining a measure of the energy released upon combustion for thus determining the combustion value of the fuel.

Advantages of such a method have already been explained in the foregoing with reference to the device.

The method according to the invention in particular comprises the step of determining at least one parameter by means of the flow measurement unit, for example of the Coriolis type. Said parameter is preferably the density, but it may also be the mass flow, or another parameter, or a combination thereof.

According to the invention it is also conceivable that the supply of the fuel to be measured and the oxygen-containing gas to the combustion chamber takes place continuously.

In another embodiment, the supply of the fuel to be measured and the oxygen-containing gas to the combustion chamber takes place periodically. Thus, combustion takes place periodically, resulting in a temperature increase, whereupon no fuel is supplied anymore and heat may thus be lost. This means that the temperature of the system can be readily kept under control. In addition to that, the time effects that occur in the temperature increase may be of service in determining dynamic effects of the heat transport in the sensor and be used, for example, for calibration purposes.

This may for example mean that the ratio between the duration between two successive supply periods on the one hand and the duration of the supply during a period on the other hand is greater than 1, preferably ranging between 5 and 15, for example between 9 and 11.

The duration of the supply of the fuel to be measured during a period may be about 10 seconds. With the ratio as described above, i.e. the period during which no fuel is supplied or, in other words, the period between two successive supply periods, can be greater than 10 seconds, preferably ranging between 50 and 150 seconds, for example between 90 and 110 seconds.

It is furthermore conceivable if the method comprises the step of measuring the amount of residual oxygen in the combusted fuel.

Figure 2:
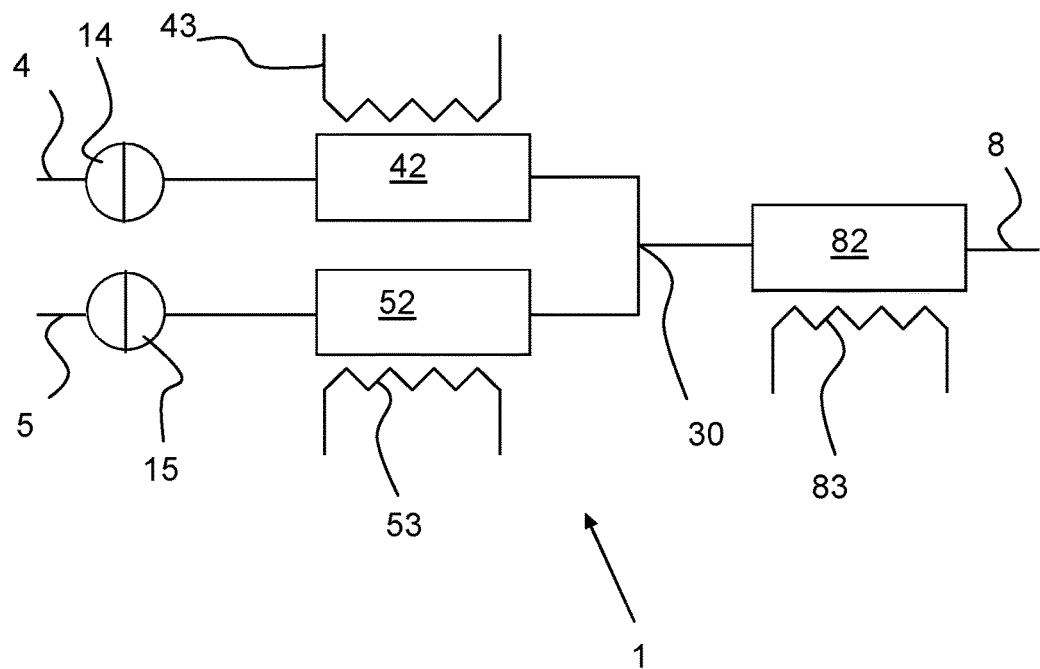
Figure 3:
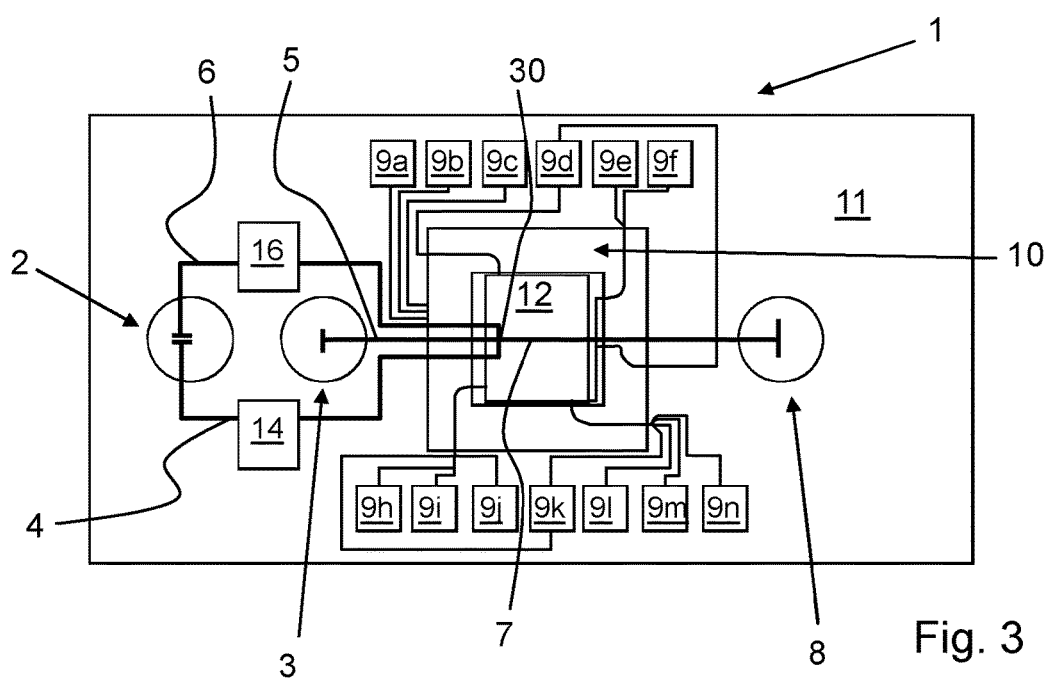

The invention will be explained in more detail below with reference to several figures, which show a possible embodiment of the invention. In the drawing:
FIG. 1 is a perspective view of the device according to the present invention;
FIG. 2 is a schematic view of the device according to the present invention;
FIG. 3 is a schematic view of an embodiment of the device according to the present invention.

FIG. 1 shows a device 1 for determining the combustion value of a fuel. The device comprises a fuel inlet 40 with an intake opening, which leads to the device 1 via an intermediate element 41. The fuel inlet 40 can be connected to, for example, a container for the fuel (whether or not under pressure) for thus supplying the fuel. In a similar manner, the device comprises a gas inlet 50, which also leads to the device 1 via an intermediate element 51. The gas inlet 50 can be used for supplying an oxygen-containing gas, such as air or oxygen, to the device, for example in that the gas inlet 50 is connected to a container for the oxygen-containing gas. The fuel and the oxygen-containing gas are supplied to a system chip 1 with a silicon substrate provided on a carrier 11. The system chip is provided with a few separated channels 4, 5, which function to transport the fuel and the oxygen-containing gas therethrough. In the system chip 1, a flow measurement unit 14, 15, a flow measurement unit of the Coriolis type in the illustrated embodiment, is provided for the fuel channel 4 and the gas channel 5, respectively. Downstream thereof, further channels 21, 22 are provided, which converge at the location of a mixing unit 30, where the fuel and the oxygen-containing gas are mixed. Downstream of the mixing channel, a combustion space 7 is provided, where the combustion takes place. Via a downstream channel 23, flue gas can be discharged to a gas outlet 8, where it can be exhausted via a tube 80.

The system chip 1 is provided with an opening 10, in which a silicon nitride flow tube 21, 22, 23 is present, which silicon nitride flow tube has two ends, which each merge into a silicon nitride-coated channel in the silicon substrate 11 via a wall of the opening. In the opening 10, an island 12 is thus formed, as it were, on which the combustion chamber is situated. The combustion chamber 7 is thus thermally insulated within the opening 10 of the system chip 1.

FIG. 2 is a schematic top plan view of an embodiment of the device 1 according to the invention. In this figure, a fuel inlet 4 and a gas inlet 5 for the oxygen-containing gas are shown again. The two inlets 4, 5 open into a flow measurement unit 14, 15, respectively, for measuring the flow rate and/or the density of the fluid. In a preferred embodiment, the flow measurement unit is of the Coriolis type. Downstream thereof, heating elements 43, 53, respectively, are provided which each heat a part 42, 52 of the flow tubes so as to thus increase the temperature of the fuel and of the oxygen-containing gas in a first step. The two individual flow tubes converge in a T-junction 30 or mixing element, where the fuel is mixed with the oxygen-containing gas. Downstream thereof, a further heating element 83 is provided for heating the mixture of fuel and the oxygen-containing gas so as to thus initiate the combustion in the combustion chamber 82. The flue gas can subsequently be discharged via the gas outlet 8.

In the embodiment shown in FIG. 2, it is conceivable that the combustion chamber 82 forms part of a system chip, and that the flow measurement units 14, 15 are provided separately therefrom as separate units. Thus it is possible, for example, to use commercially available flow measurement units, such as CORI-FLOW mass flow meters from the firm of Bronkhorst. Additionally it is conceivable that, similarly to FIG. 1, the flow measurement units and the combustion chamber form part of one integral system chip or are provided on a plurality of individual system chips.

FIG. 3 shows an alternative embodiment of the device 1, in which like parts are indicated by like numerals. The device 1 again comprises a system chip 11, which is provided with an opening 10, within which the thermally insulated combustion unit 12 is present. The device 1 now comprises two inlets 2 for the oxygen-containing gas in the form of a first tubular channel 4 and a second tubular channel 6. In said channels, a first flow measurement unit 14 and a second flow measurement unit 16, respectively, are provided, which flow measurement units are preferably of the Coriolis type. The device 1 further comprises an inlet 3 for the fuel, in which a flow measurement unit (not shown for the sake of clarity), preferably of the Coriolis type, is provided. The flow measurement unit is preferably designed for measuring the density and/or the flow rate of the fluid in question.

Downstream of the inlets 2, 3, at the location of the thermally insulated island 12, the channels converge at the location of a mixing unit 30. Located downstream thereof is the combustion space 7, which is configured as a channel in the illustrated embodiment.

On the system chip, various so-called bond pads 9a-9n or bonding surfaces are furthermore provided, which bond pads can be used, for example, for connection to a heating element, a temperature measuring element, an oxygen sensor or any other components that may be desired. Such bond pads 9a-9n are known per se to the skilled person. In the illustrated embodiment, the bond pads 9a-9f are connected to platinum heating elements, by means of which also the temperature can be measured. The bond-pads 9h-9n are connected to temperature sensors in the illustrated embodiment. An oxygen sensor (not shown) is disposed in or near the outlet 8 for measuring the residual oxygen, although it is conceivable that said oxygen sensor does not form an integral part of the device but is connected to the outlet 8 as a separate part.

The skilled person will appreciate that in the foregoing the invention has been explained with reference to a preferred embodiment of the invention. The invention is not limited thereto, however. Various modifications are conceivable within the framework of the invention. The scope of the protection being sought is defined in the appended claims.

The invention claimed is:

1. A device for determining the combustion value of a fuel, the device comprising:
   a fuel inlet with an intake opening for supplying the fuel to be measured to the device;
   a gas inlet with an intake opening for supplying an oxygen-containing gas to the device;
   a combustion unit connected to the fuel inlet and the gas inlet, the combustion unit comprising a combustion chamber for chemically reacting the fuel to be measured with the oxygen containing gas in a combustion reaction therein;
   a gas outlet connected to the combustion chamber for discharging waste gases produced in the combustion reaction;
   means for measuring at least a measure of the amount of energy released by the combustion reaction;
   a flow measurement unit disposed between the intake opening of the fuel inlet and the combustion chamber; and
   a system chip with a silicon substrate provided on a carrier, the system chip comprising an opening within which a silicon nitride flow tube is present, the silicon nitride flow tube having two ends each of which merge, via a wall of the opening, into a silicon nitride-coated channel in the silicon substrate, wherein the silicon nitride flow tube is present in the combustion unit.

2. A device according to claim 1, wherein the flow measurement unit is of the Coriolis type and determines the density and/or the flow rate of the fuel to be measured.

3. A device according to claim 1, wherein the device is designed for determining the combustion value of a gaseous and/or a liquid fuel.

4. A device according to claim 1, wherein the device comprises means for determining the Wobbe index of the fuel.

5. A device according to claim 1, wherein the means for measuring at least a measure of the amount of energy released by the combustion comprises a temperature measuring element disposed on or near the combustion unit.

6. A device according to claim 1, further comprising a flow measurement unit disposed between the intake opening of the gas inlet and the combustion chamber for determining the density and/or the flow rate of the oxygen-containing gas.

7. A device according to claim 1, further comprising a heating element for increasing the temperature of at least the fuel to be measured before it reaches the combustion chamber.

8. A device according to claim 2, wherein the silicon nitride flow tube is present in the flow measurement unit.

9. A device according to claim 1, wherein the silicon nitride flow tube comprises the combustion chamber.

10. A device according to claim 9, wherein the combustion chamber is thermally insulated within the opening of the system chip.

11. A device according to claim 1, wherein the device comprises a mixing element for mixing the fuel to be measured and the oxygen-containing gas.

12. A device according to claim 1, wherein an oxygen sensor is provided downstream of the combustion chamber for measuring the amount of residual oxygen in the combustion gas.

13. A device according to claim 1, wherein the device comprises a catalyst element.

14. A method for determining the combustion value of a fuel, using a device according to claim 1, comprising the steps of:
    supplying a fuel to be measured to the fuel inlet;
    determining the flow rate of the fuel to be measured using the flow measurement unit;
    supplying an oxygen-containing gas to the gas inlet;
    supplying the fuel to be measured and the oxygen-containing gas to the combustion chamber of the combustion unit;
    chemically reacting the fuel to be measured with the oxygen-containing gas in a combustion reaction; and
    determining the combustion value of the fuel by measuring the energy released in the combustion reaction.

15. A method according to claim 14, wherein the supplying the fuel to be measured and the oxygen-containing gas to the combustion chamber of the combustion unit takes place continuously.

16. A method according to claim 15, wherein the supplying the fuel to be measured and the oxygen-containing gas to the combustion chamber of the combustion unit takes place periodically.

17. A method according to claim 16, wherein the ratio between the duration between two successive supply periods and the duration of the supply during a period is selected from greater than 1, between 5 and 15, and between 9 and 11.

18. A method according to claim 17, wherein the duration of the supply during a period is about 10 seconds.

19. A method according to claim 16, wherein the method comprises the step of measuring the amount of residual oxygen in the waste gas.

\* \* \* \* \*